United States Patent
Saettler et al.

(10) Patent No.: US 6,630,003 B1
(45) Date of Patent: Oct. 7, 2003

(54) COLOURING AGENTS WITH ENZYMES

(75) Inventors: Andrea Saettler, Duesseldorf (DE); Albrecht Weiss, Langenfeld (DE); David Rose, Hilden (DE); Astrid Kleen, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/807,644

(22) PCT Filed: Oct. 5, 1999

(86) PCT No.: PCT/EP99/07368

§ 371 (c)(1), (2), (4) Date: Aug. 21, 2001

(87) PCT Pub. No.: WO00/21497

PCT Pub. Date: Apr. 20, 2000

(30) Foreign Application Priority Data

Oct. 14, 1998 (DE) .......................................... 198 47 276

(51) Int. Cl.⁷ ................................................. A61K 7/13
(52) U.S. Cl. ...................... 8/405; 8/406; 8/407; 8/411; 8/412; 8/421; 424/94.1; 424/94.4
(58) Field of Search .......................... 8/405, 406, 407, 8/411, 412, 421; 424/94.1, 94.4

(56) References Cited

U.S. PATENT DOCUMENTS

| | | | |
|---|---|---|---|
| 4,865,774 A | 9/1989 | Fabry et al. .................. 252/554 |
| 4,931,218 A | 6/1990 | Schenker et al. ............. 252/551 |
| 5,294,726 A | 3/1994 | Behler et al. ................. 554/98 |
| 5,534,267 A | 7/1996 | Neunhoeffer et al. ........ 424/701 |
| 5,849,041 A | * 12/1998 | Kunz et al. .................... 8/408 |
| 6,099,590 A | 8/2000 | Maubru ......................... 8/401 |
| 6,099,592 A | 8/2000 | Vidal et al. .................... 8/409 |

FOREIGN PATENT DOCUMENTS

| | | |
|---|---|---|
| DE | 2155390 | 5/1972 |
| DE | 37 23 354 | 1/1989 |
| DE | 37 25 030 | 2/1989 |
| DE | 39 26 344 | 2/1991 |
| DE | 195 45 729 | 6/1997 |
| DE | 197 13 852 | 10/1998 |
| EP | 0 310 675 | 4/1989 |
| EP | 0 548 620 | 6/1993 |
| EP | 0 740 931 | 11/1996 |
| EP | 0 795 313 | 9/1997 |
| FR | 2768618 | 3/1999 |
| GB | 1321560 | 6/1973 |
| WO | WO94/08970 | 4/1994 |

OTHER PUBLICATIONS

The Science of Hair Care, Chapter 7, pp. 235–261, published as vol. 7 of Dermatology, Marcel Dekker Inc., NY/Basle (1986).

The Science of Hair Care, Chapter 8, pp. 263–286 published as vol. 7 of Dermatology, Marcel Dekker Inc., NY/Basle (1986).

EU Inventory of Cosmetic Ingredients, Colipa, Mar. 1996—on diskette.

* cited by examiner

*Primary Examiner*—Yogendra N. Gupta
*Assistant Examiner*—Eisa Elhilo
(74) *Attorney, Agent, or Firm*—Stephen D. Harper; Gregory M. Hill

(57) ABSTRACT

The present invention relates to a composition for coloring keratin fibers containing at least one dye precursor and a choline-based oxidase system. The present invention also relates to a process for coloring keratin containing fibers using the composition of the present invention.

21 Claims, No Drawings

COLOURING AGENTS WITH ENZYMES

CROSS REFERENCE TO RELATED APPLICATIONS

This application is a national stage application under 35 U.S.C. §371 of international application PCT/EP99/07368 filed on Oct. 5, 1999, the international application not being published in English. This application also claims priority under 35 U.S.C. §119 to DE 198 47 276.5 filed on Oct. 14, 1998.

FIELD OF THE INVENTION

This invention relates to compositions containing a special enzyme system for coloring keratin fibers, to their use and to corresponding processes for coloring keratin fibers.

BACKGROUND OF THE INVENTION

By virtue of their intensive colors and good fastness properties, so-called oxidation colorants play a prominent role in the coloring of keratin fibers, particularly human hair. Oxidation colorants contain oxidation dye precursors, so-called primary intermediates and secondary intermediates. The primary intermediates form the actual dyes with one another or by coupling with one or more secondary intermediates in the presence of oxidizing agents or atmospheric oxygen.

In general, natural-looking hair colors cannot be obtained solely with a primary intermediate or with a special primary intermediate/secondary intermediate combination. In practice, therefore, combinations of various primary intermediates and/or secondary intermediates are normally used.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, 2,4,5,6-tetraaminopyrimidine, p-aminophenol, N,N-bis-(2-hydroxyethyl)-p-phenylenediamine, 2-(2,5-diaminophenyl)-ethanol, 2-(2,5-diaminophenoxy)-ethanol, 1-phenyl-3-carboxyamido4-amino-5-pyrazolone, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine, 2,5,6-triamino-4-hydroxypyrimidine and 1,3-N,N'-bis-(2'-hydroxyethyl)-N,N'-bis-(4'-aminophenyl)-diamino-2-propanol.

The secondary intermediates used are generally m-phenylenediamine derivatives, naphthols, resorcinol and resorcinol derivatives, pyrazolones and m-aminophenols. Particularly suitable secondary intermediates are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenoll, 2-methyl resorcinol, 5-methyl resorcinol and 2-methyl-4-chloro-5-aminophenol.

In principle, the color can be oxidatively developed with atmospheric oxygen. However, a chemical oxidizing agent is preferably used. Suitable oxidizing agents are persulfates, chlorites and, above all, hydrogen peroxide or addition products thereof with urea, melamine and sodium borate. A 2–9% aqueous hydrogen peroxide solution is normally used. The keratin fibers can be damaged by such high concentrations of oxidizing agent, particularly where they have already been "permed" or bleached. In some cases, skin irritation can also be caused by these high concentrations.

A significant start to solving this problem is to reduce the concentration of oxidizing agent. Accordingly, attempts have already been made on the one hand to find dye precursors which, by virtue of their chemical structure, can be oxidized even by relatively small quantities of hydrogen peroxide or by atmospheric oxygen. On the other hand, it has been proposed to use enzymes as biocatalysts which are capable of catalyzing the desired oxidation process with very little, if any, hydrogen peroxide simply in the presence of atmospheric oxygen.

DE-OS 2 155 390 describes an enzyme-activated oxidative hair coloring process in which small quantities of $H_2O_2$ are used in combination with a peroxidase enzyme. EP-A1-0 310 675 also discloses enzymatic hair treatment preparations which contain at least one dielectron-reducing oxidase that uses oxygen as acceptor. EP-B1 0 548 620 describes enzymatic hair colorants where oxidation of the dye precursors is catalyzed by the use of a peroxidase. Finally, EP-A2 0 795 313 describes enzymatic hair colorants which contain an oxygen-oxidoreductase/substrate system and a peroxidase and, as a compulsory secondary intermediate, an m-phenylenediamine derivative. However, none of these colorants has yet proved totally convincing in terms of their coloring performance (intensity, tone, brilliance, fastness properties).

Readily oxidizable dye precursors have the disadvantage, along with the enzymatic color development hitherto described, that the results they give in regard to intensity, brilliance and color fastness properties are poorer by comparison with the conventional processes.

Accordingly, the problem addressed by the present invention was to provide colorants for keratin fibers which would enable the fibers to be treated without damage and at the same time would guarantee excellent coloring performance.

It has now surprisingly been found that high-performance colorants with distinct advantages in terms of fiber and skin care are obtained if they contain at least one dye precursor, a choline-based oxidase system and at least one peroxidase.

DETAILED DESCRIPTION OF THE INVENTION

Keratin fibers in the context of the invention are understood to be pelts, wool, feathers and in particular human hair.

According to the invention, a choline-based oxidase system is understood to be choline oxidase in combination with choline as substrate. Choline is oxidized by choline oxidase in accordance with the following reaction scheme:

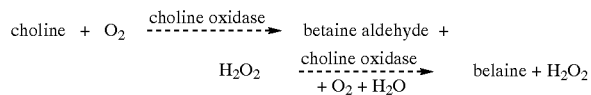

For the purposes of the present invention, choline is preferably used in the form of a salt with a physiologically compatible organic or inorganic acid. Examples of such salts are the chloride, the bromide, the iodide, the citrate, the hydrogen tartrate, the hydrogen carbonate, the methyl sulfate and the p-toluenesulfonate. Choline chloride is particularly preferred.

Choline oxidase (EC 1.1.3.17) can be obtained from various sources. One occurrence was found, for example, in human cells. Choline oxidase produced by Alcaligenes species and *Arthrobacter globiformis* is particularly preferred for the purposes of the invention. Choline oxidases are commercially available and are marketed, for example, by Sigma. According to the invention, the activity of the choline oxidase is defined as follows: one unit [1 U] of choline oxidase catalyzes the oxidation of 1 μmol of choline to betaine aldehyde in one minute at pH 8.0/37° C., 1 μmol of $H_2O_2$ being formed (according to Sigma's definition of the commercial products).

Choline oxidase is used in the compositions according to the invention in quantities of 1 to 50,000 U per 100 g of coloring preparation. Quantities of 1 to 10,000 U per 100 g of coloring preparation are preferred, the range from 400 to 5,000 U per 100 g of coloring preparation being most particularly preferred.

According to the invention, the substrate choline is used in quantities of 1 to 5% by weight, based on the coloring preparation as a whole.

Besides the choline-based oxidase system, the compositions according to the invention also contain a peroxidase (EC 1.11.1.7). The peroxidases may be obtained from animals, plants or fungi. Vegetable peroxidases and fungus-based peroxidase can be particularly preferred for the purposes of the invention, soybean peroxidase being most particularly preferred.

In another embodiment of the present invention, peroxidases with a minimal catalase content, for example horse radish peroxidase, are preferably used.

According to the invention, the activity of the peroxidase is defined as follows: 1 unit [1 U] of peroxidase forms 1.0 mg of purpurogallin from pyrogallol in 20 seconds at pH 6.0/20° C. (according to Sigma's definition of the commercial products).

According to the invention, the peroxidase is used in a quantity of 1 to 100,000 U. Quantities of 1 to 10,000 U are preferred, a quantity of 1 to 500 U being most particularly preferred. The quantities mentioned are all based on 100 g of coloring preparation.

The compositions according to the invention are distinguished by their hair- and skin-preserving effect. Hair treated in accordance with the invention has greater smoothness, higher tensile strength and lower porosity than hair colored by conventional coloring techniques.

In a first embodiment of the present invention, the dye precursor may be an oxidation dye precursor of the primary intermediate type. However, several primary intermediates may also be used in the compositions according to the invention.

According to the invention, preferred primary intermediates are p-phenylenediamine, p-toluylenediamine, p-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxyethylaminomethyl-4-aminophenol, 4,4'-diaminodiphenylamine, 4-amino-3-fluorophenol, 2-aminomethyl-4-aminophenol, 2-hydroxymethyl-4-aminophenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 1,8-bis-(2,5-diaminophenoxy)-3,6-dioxaoctane, 4-amino-2-(2-hydroxyethoxy)-phenol and 4,5-diaminopyrazole derivatives according to EP 0 740 931 or WO 94/08970, for example 4,5-diamino-1-(2'-hydroxyethyl)-pyrazole.

Particularly preferred primary intermediates are p-phenylenediamine, p-toluylenediamine, p-aminophenol, 1-(2'-hydroxyethyl)-2,5-diaminobenzene, 4-amino-3-methylphenol, 2,4,5,6-tetraaminopyrimidine, 2-hydroxy-4,5,6-triaminopyrimidine, 4-hydroxy-2,5,6-triaminopyrimidine, 4,5-diamino-1-(2-hydroxyethyl)-pyrazole, 2-aminomethyl-4-aminophenol, N,N-bis-(2-hydroxyethyl)-p-phenylenediamine, 1,8-bis-(2,5-diaminophenoxy)-3,6-dioxaoctane, bis-(2-hydroxy-5-aminophenyl)-methane and o-aminophenol.

Most particularly preferred primary intermediates are 1-methyl-2,5-diaminobenzene, 4-amino-2-aminomethylphenol, p-aminophenol, 4-hydroxy-2,5,6-triaminopyrimidine, 1-(2'-hydroxyethyl)-2,5-diaminobenzene and N,N-bis-(2-hydroxyethyl)-1,4-diaminobenzene.

The compositions according to the invention may additionally contain one or more secondary intermediates for shading the color tones obtained. According to the invention, preferred secondary intermediates are 1-naphthol, pyrogallol, 1,5-, 2,7- and 1,7-dihydroxynaphthalene, o-aminophenol, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2-amino-3-hydroxypyridine, 2,6-dimethoxy-3,5-diaminopyridine, 2,6-dihydroxy-3,4-diaminopyridine, 3-amino-2-methylamino-6-methoxypyridine, 4-amino-2-hydroxytoluene, 2,6-bis-(2-hydroxyethylamino)-toluene, 2,4-diaminophenoxyethanol, 1-methoxy-2-amino-4-(2-hydroxyethylamino)-benzene, 2-methyl-4-chloro-5-aminophenol, 6-methyl-1,2,3,4-tetrahydroquinoxaline, 3,4-methylenedioxyphenol, 3,4-methylenedioxyaniline, 2,6-dimethyl-3-aminophenol, 3-amino-6-methoxy-2-methylaminophenol, 2-hydroxy-4-aminophenoxy ethanol, 2-methyl-5-(2-hydroxyethylamino)-phenol and 2,6-dihydroxy-3,4-dimethyl pyridine.

Particularly preferred secondary intermediates for the purposes of the invention are 1-naphthol, 1,5-, 2,7- and 1,7-dihydroxynaphthalene, 5-amino-2-methylphenol, resorcinol, 1,3-bis-(2,4-diaminophenoxy)-propane, 2,4-dichloro-3-aminophenol, 4-chlororesorcinol, 2-amino-3-hydroxypyridine, 2,6-dimethoxy-3,5-diaminopyridine, 2-chloro-6-methyl-3-aminophenol, 2-methyl-4-chloro-5-aminophenol, 2-methyl resorcinol, 5-methyl resorcinol, 2,5-dimethyl resorcinol, 2,6-bis-(2-hydroxyethylamino)-toluene, 2,6-dihydroxy-3,4-diaminopyridine, 3-amino-2-methylamino-6-methoxypyridine, 2,4-diaminophenoxy ethanol, 1-methoxy-2-amino-4-(2-hydroxyethylamino)-benzene, 6-methyl-1,2,3,4-tetrahydroquinoxaline, 3,4-methylenedioxy aniline, m-aminophenol, o-aminophenol and 2-chlororesorcinol.

Most particularly preferred secondary intermediates are 2,4-diaminophenoxy ethanol, 2-chloro-6-methyl-3-aminophenol, 5-amino-2-methylpenol, 1,3-bis-(2,4-diaminophenoxy)-propane, 2-methyl resorcinol and 1-methoxy-2-amino-4-(2-hydroxyethylamino)-benzene.

The primary and secondary intermediates are normally used in free form. However, compounds containing amino groups may preferably be used in salt form, more particularly in the form of the hydrochlorides and sulfates.

The following primary intermediate/secondary intermediate combinations have proved to be particularly suitable for the purposes of the invention:

4-aminophenol/5-amino-2-methylphenol
1-methyl-2,5-diaminobenzene/2,4-diaminophenoxyethanol
4-amino-2-aminomethylphenol/2-chloro-6-methyl-3-aminophenol
4-amino-2-aminomethylphenol/2,4-diaminophenoxy ethanol
1-methyl-2,5-diaminobenzene/5-amino-2-methylphenol
1-methyl-2,5-diaminobenzene/1,3-bis-(2,4-diaminophenoxy)-propane
4-hydroxy-2,5,6-triaminopyridine/2-methylresorcinol
1-(β-hydroxyethyl)-2,5-diaminobenzene/2,4-diaminophenoxy ethanol
N,N-bis-(β-hydroxyethyl)-1,4-diaminobenzene/1-methoxy-2-amino-4-(2-hydroxyethylamino)-benzene.

The hair colorants according to the invention contain both the primary intermediates and the secondary intermediates in a quantity of preferably 0.005 to 20% by weight and more preferably 0.1 to 5% by weight, based on the oxidation colorant as a whole. The primary intermediates and secondary intermediates are generally used in a substantially equimolar ratio to one another. Although it has proved to be of advantage to use the primary and secondary intermediates in an equimolar ratio, there is no disadvantage in using individual oxidation dye precursors in a certain excess so that primary intermediates and secondary intermediates may be present in a molar ratio of 1:0.5 to 1:3 and more particularly 1:1 to 1:2.

In a second embodiment of the present invention, the dye precursor may be a derivative of indoline. Preferred examples are derivatives of 5,6-dihydroxyindoline corresponding to formula (Ia):

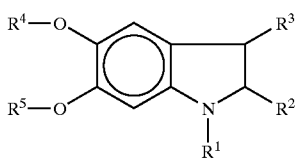

(Ia)

in which—independently of one another —$R^1$ is hydrogen, a $C_{1-4}$ alkyl group or a $C_{1-4}$ hydroxyalkyl group, $R^2$ is hydrogen or a —COOH group, the —COOH group optionally being present as a salt with a physiologically compatible cation, $R^3$ is hydrogen or a $C_{1-4}$ alkyl group, $R^4$ is hydrogen, a $C_{1-4}$ alkyl group or a group —CO—$R^6$, where $R^6$ is a $C_{1-4}$ alkyl group, and $R^5$ is one of the groups mentioned for $R^4$, or a physiologically compatible salt of these compounds with an organic or inorganic acid.

In a third embodiment of the present invention, the dye precursor may be a derivative of indole. Preferred examples are derivatives of 5,6-dihydroxyindole corresponding to formula (Ib):

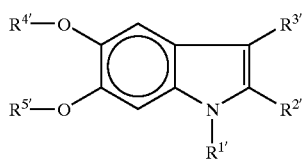

(Ib)

in which—independently of one another —$R^{1'}$ is hydrogen, a $C_{1-4}$ alkyl group or a $C_{1-4}$ hydroxyalkyl group, $R^{2'}$ is hydrogen or a —COOH group, the —COOH group optionally being present as a salt with a physiologically compatible cation, $R^{3'}$ is hydrogen or a $C_{1-4}$ alkyl group, $R^{4'}$ is hydrogen, a $C_{1-4}$ alkyl group or a group —CO—$R^{6'}$, where $R^{6'}$ is a $C_{1-4}$ alkyl group, and $R^{5'}$ is one of the groups mentioned for $R^{4'}$, or a physiologically compatible salt of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-aminoindoline. Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

5,6-Dihydroxyindoline and 5,6-dihydroxyindole are most particularly preferred.

In a first variant of the embodiments described above, the compositions are formulated in such a way that they only contain indole and/or indoline derivatives as oxidation dye precursors and are free from typical oxidation dye precursors of the primary intermediate/secondary intermediate type.

In a second variant of the embodiments described above, the compositions according to the invention also contain typical oxidation dye precursors of the primary intermediate/secondary intermediate type in addition to the indole and/or indoline derivatives. In this variant, the indoline or indole derivative may preferably be used in combination with one or more secondary intermediates in hair colorants. Attention is specifically drawn at this juncture to the secondary intermediates mentioned above as preferred.

In another preferred embodiment of the invention, the indoline or indole derivative may be used in combination with at least one amino acid or one oligopeptide in hair colorants. The amino acid is advantageously an α-amino acid; most particularly preferred α-amino acids are arginine, ornithine, lysine and histidine.

In another preferred embodiment, the hair colorants according to the invention may contain typical substantive dyes in addition to the dye precursors to further modify the shades. Substantive dyes are normally nitrophenylendiamines, nitroaminophenols, azo dyes, anthraquinones or indophenols. Preferred substantive dyes are the compounds known under the International names or trade names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6- chloro-4-nitrophenol, 4-ethylamino-3-nitrobenzoic acid and 2-chloro-6-ethylamino-1-hydroxy-4-nitrobenzene.

The colorants according to the invention of this embodiment contain the substantive dyes in a quantity of preferably 0.01 to 20% by weight, based on the colorant as a whole.

The compositions according to the invention may also contain naturally occurring dyes such as, for example, henna red, henna neutral, henna black, camomile blossom, sandalwood, black tea, black alder bark, sage, logwood, madder root, catechu, sedre and alkanet.

The dye precursors or the substantive dyes do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting compositions according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basel, 1986, and to the "Europäische Inventar der Kosmetik-Rohstoffe" published by the Europäische Gemeinschaft and available in disk form from the Bundesverband Deutscher Industrie- und Handelsunternehmen für Arzneimittel, Reformwaren und Körperpflegemittel d.V., Mannheim.

Hair colorants based on the choline oxidase system with a pH of 7 to 10 and more particularly 8 to 9 are preferred. It has been found in accordance with the invention that particularly intensive and brilliant colors are obtained if the composition has a pH value of about 8.3. The pH value of the hair colorant is preferably adjusted with a tris-(hydroxymethyl)-aminomethane/potassium chloride buffer system.

Besides the choline oxidase system according to the invention, the colorants according to the invention may contain other oxidases with their respective substrates. Examples are glucose oxidase, alcohol oxidase, pyruvate oxidase, oxalate oxidase, cholesterol oxidase, uricase, lactate oxidase, xanthine oxidase, pyranose oxidase, glycerol oxidase and galactose oxidase. Compositions which contain glucose oxidase and/or xanthine oxidase and their respective substrates in addition to the choline oxidase system are preferred.

To produce the colorants according to the invention, the dye precursors may be incorporated in a suitable water-containing carrier. For coloring hair, such carriers are, for example, creams, emulsions, gels or even surfactant-containing foaming solutions, for example shampoos, foam aerosols or other formulations suitable for application to the hair.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. If necessary, the expert may check the various surfactants for any effects on the activity of the enzyme system according to the invention by carrying out simple preliminary tests.

In one preferred embodiment of the present invention, a combination of anionic and nonionic surfactants or a combination of anionic and amphoteric surfactants is used in the compositions for coloring keratin fibers.

However, it has proved to be of advantage in individual cases to select the surfactants from amphoteric or nonionic surfactants because they generally have less influence on the coloring process according to the invention.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps), ether carboxylic acids corresponding to the formula $R-O-(CH_2-CH_2O)_x-CH_2-COOH$, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula $R-O(CH_2-CH_2O)_x-SO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

Ampholytic surfactants are surface-active compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl amino-propionate, cocoacyl aminoethyl aminopropionate and C$_{12\text{-}18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, C$_{12\text{-}22}$ fatty acid monoesters and diesters of products of the addition of 1 to 30 moles of ethylene oxide onto glycerol, C$_{8\text{-}22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides and amine oxides.

Alkyl polyglycosides corresponding to formula (II):

in which R$^6$ is an alkyl group containing 8 to 22 carbon atoms, Z is a mono- or oligosaccharide and x is a number of 1.1 to 5, are particularly preferred nonionic surfactants. These compounds are characterized by the following parameters.

The alkyl group R$^6$ contains 8 to 22 carbon atoms and may be both linear and branched. Primary linear and 2-methyl-branched aliphatic groups are preferred. Corresponding alkyl groups are, for example, 1-octyl, 1-decyl, 1-lauryl, 1-myristyl, 1-cetyl and 1-stearyl. 1-Octyl, 1-decyl, 1-lauryl and 1-myristyl are particularly preferred. Where so-called "oxo alcohols" are used as starting materials, compounds with an odd number of carbon atoms in the alkyl chain predominate.

The alkyl polyglycosides usable in accordance with the invention may contain only one particular alkyl group R$^6$. Normally, however, these compounds are produced from natural fats and oils or mineral oils. In this case, the alkyl groups R$^6$ are mixtures corresponding to the starting compounds of to the particular working up of these compounds.

Particularly preferred alkyl polyglycosides are those in which R$^6$ consists essentially of C$_8$ and C$_{10}$ alkyl groups,
essentially of C$_{12}$ and C$_{14}$ alkyl groups,
essentially of C$_8$ to C$_{16}$ alkyl groups or
essentially of C$_{12}$ to C$_{16}$ alkyl groups.

Any mono- or oligosaccharides may be used as the sugar unit Z. Sugars containing 5 or 6 carbon atoms and the corresponding oligosaccharides are normally used. Such sugars are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose. Glucose is particularly preferred.

The alkyl polyglycosides usable in accordance with the invention contain on average 1.1 to 5 sugar units. Alkyl glycosides with x-values of 1.3 to 2 are preferred. Alkyl glycosides in which x is 1.4 to 1.6 are most particularly preferred.

Amine oxides corresponding to general formula (VI):

in which R$^7$ is a branched or unbranched C$_{8\text{-}18}$ alkyl chain and R$^8$ and R$^9$ independently of one another represent a C$_{1\text{-}3}$ alkyl group or a C$_{1\text{-}3}$ hydroxyalkyl group, are also preferred.

Another amine oxide usable in accordance with the invention is the amine oxide WS 35 marketed by Tego® Cosmetics in which R$^8$ and R$^9$ represent methyl groups and R$^7$ is a cocoacyl amidopropyl group.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the INCI name of Cocamidopropyl Betaine.

Examples of the cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the products marketed under the name of Dehyquart®, such as Dehyquart AU-46, are also readily biodegradable.

One example of a quaternary sugar derivative suitable for use as a cationic surfactant is the commercially available product Glucquat® 100 (INCI name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example,

- nonionic polymers such as, for example, vinyl pyrrolidone/vinyl acrylate copolymers, polyvinyl pyrrolidone and vinyl pyrrolidone/vinyl acetate copolymers and polysiloxanes,
- cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol,
- zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers,
- anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers,
- thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants, such as glucose, maleic acid and lactic acid,
- hair-conditioning compounds, such as phospholipids, for example soybean lecithin, egg lecithin and kephalins, and also silicone oils,
- protein hydrolyzates, more particularly elastin, collagen, keratin, milk protein, soybean protein and wheat protein hydrolyzates, condensation products thereof with fatty acids and quaternized protein hydrolyzates,
- perfume oils, dimethyl isosorbide and cyclodextrins,
- solubilizers, such as ethanol, isopropanol, ethylene glycol, propylene glycol, glycerol and diethylene glycol,
- antidandruff agents, such as Piroctone Olamine and Zinc Omadine,
- other substances for adjusting the pH value,
- active principles, such as panthenol, pantothenic acid, allantoin, pyrrolidone carboxylic acids and salts thereof, plant extracts and vitamins, amino acids
- cholesterol,
- UV filters,
- consistency factors, such as sugar esters, polyol esters or polyol alkyl ethers,
- fats and waxes, such as spermaceti, beeswax, montan wax, paraffins, fatty alcohols and fatty acid esters,
- fatty acid alkanolamides,
- complexing agents, such as EDTA, NTA and phosphonic acids,
- swelling and penetration agents, such as glycerol, propylene glycol monoethyl ether, carbonates, hydrogen carbonates, guanidines, ureas and primary, secondary and tertiary phosphates,
- opacifiers, such as latex,
- pearlizers, such as ethylene glycol mono- and distearate,
- propellents, such as propane/butane mixtures, $N_2O$, dimethyl ether, $CO_2$ and air and
- antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

The enzyme preparation is preferably mixed with the preparation of dye precursors immediately before coloring of the hair. The application temperatures may be in the range from 15 to 40° C. After a contact time of about 5 to 30 minutes, the hair colorant is removed from the hair to be colored by rinsing. There is no need for the hair to be washed with a shampoo where a carrier of high surfactant content, for example a coloring shampoo, has been used.

To accelerate the coloring process, an aqueous solution of the oxidase system may preferably be separately adjusted to the required pH before mixing with the coloring preparation and preincubated for 30 mins. at 37° C., for example in a shaking hood. The preincubation mixture is then incorporated in the coloring cream. Finally, the peroxidase is added.

In another embodiment of the invention, the enzyme preparation is preferably formulated without antioxidants and/or complexing agents because they can block the effect of the enzymes.

The following Examples are intended to illustrate the invention.

EXAMPLES

Example 1

Coloring with the Choline Oxidase System According to the Invention

1. Preparation of the coloring cream (a) Cream base (mixture A)

| | |
|---|---|
| Hydrenol ® D[1] | 8.50 g |
| Lorol ® techn.[2] | 2.00 g |
| Eumulgin ® B2[3] | 0.75 g |
| Texapon ® NSO[4] | 20.00 g |
| Dehyton ® K[5] | 12.50 g |
| Water | 30.00 g |

[1]$C_{16-18}$ fatty alcohol (INCI name: Cetearyl Alcohol) (HENKEL)
[2]$C_{12-18}$ fatty alcohol (INCI name: Coconut Alcohol) (HENKEL)
[3]Cetylstearyl alcohol containing ca. 20 EO units (INCI name: Ceteareth-20) (HENKEL)
[4]Lauryl ether sulfate, sodium salt (ca. 27.5% active substance; INCI name: Sodium Laureth Sulfate) (HENKEL)
[5]N,N-dimethyl-N-($C_{8-18}$-cocoamidopropyl)-ammonium acetobetaine (ca. 30% active substance; INCI name: Aqua (Water), Cocamidopropyl Betaine) (HENKEL)

The substances Hydrenol D, Lorol and Eumulgin B2 were melted at 80° C., mixed with the water heated to 80° C. containing Texapon NSO and Dehyton T and emulsified with vigorous stirring. The emulsion was then cooled with gentle stirring.

(b) Coloring preparations

Mixture B1

| | |
|---|---|
| 4-aminophenol | 0.27 g (0.0025 mole) |
| ammonium hydroxide[1] | to pH 7.0 |
| water | 10 ml |

[1]A commercial ammonium hydroxide solution (Sigma) containing ca. 30% ammonia was mixed with twice-distilled water in a ratio of 1:10

Mixture B2

| | |
|---|---|
| 5-amino-2-methyl phenol | 0.31 g (0.0025 mole) |
| ammonium hydroxide | to pH 7.0 |
| water | 10 ml |

The dye precursors were each dissolved in 10 ml water and the pH of the solutions was adjusted with ammonium hydroxide.

The dye preparations (mixtures B1 and B2) were added to 25 g of the cream base (mixture A) melted at 80° C. and the pH was optionally adjusted to a value of 7 with an aqueous HCl solution or with ammonium hydroxide. The cream was made up with water to 50 g and cooled with stirring to 30° C.

2. Preparation of the Enzyme Solutions (a) Peroxidase Solution (0.41 U/ml)

Powder-form peroxidase from soya beans (Sigma: Catalog No. P-1432) was used to prepare the peroxidase solution. The activity of the peroxidase is defined thus: one unit [1U] peroxidase forms 1.0 mg purpurogallin from pyrogallol in 20 seconds at pH 6.0/20° C.

Since the activity based on the weight (U/g) of the peroxidase varies from batch to batch in the commercial products, the preparation of the solution is dependent on the activity of the peroxidase supplied.

Peroxidase with an activity of 73 U/mg was used. 1 g of this peroxidase was dissolved in 1 ml of twice-distilled water; 28.3 µl of this solution were removed and made up to 5 ml with twice-distilled water. The solution was adjusted to pH 7 with ammonium hydroxide. The solution thus contains per milliliter the quantity of peroxidase which has an activity of 0.41 U under the conditions mentioned above.

(b) Choline Oxidase Solution (33.2 U/ml)

Powder-form choline oxidase from Alcaligenes species (Sigma: Catalog No. C-5896) was used to prepare the choline oxidase solution. The activity of the choline oxidase is defined thus: one unit [1 U] of choline oxidase forms 1 µmol $H_2O_2$ in 1 minute at pH 8.0/37° C. by oxidation of 1 µmol choline to betaine aldehyde.

Since the activity based on the weight (U/g) of the choline oxidase varies from batch to batch in the commercial products, the preparation of the solution is dependent on the activity of the choline oxidase supplied.

Choline oxidase with an activity of 14 U/mg was used. 15 mg of this choline oxidase were dissolved in 5 ml of twice-distilled water; 3.952 ml of this solution were removed and made up to 5 ml with twice-distilled water. The solution was adjusted to pH 7 with ammonium hydroxide. The solution thus contains per milliliter the quantity of choline oxidase which has an activity of 33.2 U under the conditions mentioned above.

(c) Choline Chloride Solution 3.36 g of choline chloride were dissolved in 20 ml of twice-distilled water. The pH value of the solution was adjusted to 7 with ammonium hydroxide.

3. Incubation Mixture 2.5 ml of the aqueous choline chloride solution (according to 2c) were mixed with 2.5 ml of the aqueous choline oxidase solution (33.2 U/ml, according to 2b) and the pH was adjusted to 7 with ammonium hydroxide. The resulting solution was then placed in a crystallization dish and pre-incubated for 30 mins. at 37° C. in a shaking hood (100 r.p.m.).

4. Coloring of Hair 8 g of the cooled coloring cream (according to 1) were stirred with 4 ml of the incubation mixture (according to 3). 4 ml of a soya bean peroxidase solution (0.41 U/ml) were then added. 100 g of the ready-to-use coloring system contain the quantity of choline oxidase which has an activity of 415 U under the conditions mentioned above. In addition, 100 g of the ready-to-use coloring system contains the quantity of soya bean peroxidase which has an activity of 10.3 U under the conditions mentioned above.

A 6 cm long hair tress weighing 0.5 g (Kerling, 80% grey) was immersed in this coloring system for 10 minutes. The color was then further developed in air for 35 mins. in a Petri dish. The hair was then rinsed with luke-warm water and dried in air.

The color of the tress was evaluated as 6B6, grey-orange, according to the color scale in the color catalog (Taschenlexikon der Farben, A. Kornerup and J. H. Wansche, Muster-Schmidt-Verlag, 3rd Unrevised Edition, 1981).

5. Comparison Test

To determine the influence of the enzymes, a 6 cm long hair tress weighing 0.5 g (Kerling, 80% grey) was immersed for 10 minutes in the coloring cream according to 1 without addition of the enzyme solutions. The color was then further developed in air for 35 mins. in a Petri dish. The hair was then rinsed with luke-warm water and dried in air. The color of the tress, which developed without the influence of the enzymes, was evaluated as 4A5, butter yellow.

Example 2

Comparison of Choline Oxidase System and Glucose Oxidase System

1. Preparation of the Coloring Cream

The coloring cream of Example 1 adjusted to pH 8.3 with ammonium hydroxide was used.

2. Preparation of the Enzyme Solutions

The peroxidase solution of Example 1, point 2a, was used. In addition, the following solutions were prepared:

(a) Buffer Solution 0.01 mol tris(hydroxymethyl)aminomethane and 0.134 mol potassium chloride were dissolved in 950 ml water. The resulting solution was adjusted to pH 8.3 with 1-molar hydrochloric acid and made up to 1 liter.

(b) Choline Oxidase Solution (33.2 U/ml), Invention

Powder-form choline oxidase from Alcaligenes species (Sigma: Catalog No. C-5896) was used to prepare the choline oxidase solution. The activity of the choline oxidase is defined thus: one unit [1 U] of choline oxidase forms 1 $\mu$mol $H_2O_2$ in 1 minute at pH 8.0/37° C. by oxidation of 1 $\mu$mol choline to betaine aldehyde.

Since the activity based on the weight (U/g) of the choline oxidase varies from batch to batch in the commercial products, the preparation of the solution is dependent on the activity of the choline oxidase supplied.

Choline oxidase with an activity of 14 U/mg was used. 15 mg of this choline oxidase were dissolved in 5 ml of buffer solution; 3.952 ml of this solution were removed and made up to 5 ml with the buffer solution. The solution had a pH of 8.3. The solution contains per milliliter the quantity of choline oxidase which has an activity of 33.2 U under the conditions mentioned above.

(c) Choline Chloride Solution, Invention 1.68 g of choline chloride were dissolved in 10 ml of the buffer solution. The pH value of the solution was 8.3.

(d) Glucose Oxidase Solution (33.2 U/ml), Comparison System

Powder-form glucose oxidase from *Aspergillus niger* (Sigma: Catalog No. G-7141) was used to prepare the glucose oxidase solution. The activity of the glucose oxidase is defined thus: one unit [1 U] of glucose oxidase forms 1 $\mu$mol $H_2O_2$ in 1 minute at pH 5.1/35° C. by oxidation of 1 $\mu$mol β-D-glucose to D-gluconolactone.

Since the activity based on the weight (U/g) of the glucose oxidase varies from batch to batch in the commercial products, the preparation of the solution is dependent on the activity of the glucose oxidase supplied.

Glucose oxidase with an activity of 150 U/mg was used. 1 mg of this glucose oxidase was dissolved in 5 ml of buffer solution; 798 $\mu$l of this solution were removed and made up to 5 ml with buffer solution. The solution had a pH of 8.3. The solution contains per milliliter the quantity of glucose oxidase which has an activity of 33.2 U under the conditions mentioned above.

(e) Glucose Solution, Comparison System 1.376 g of D-(+)-glucose monohydrate were dissolved in 10 ml of buffer solution. The pH of the solution was 8.3.

3. Incubation Mixture (a) Choline Oxidase System, Invention 2.5 ml of the aqueous choline chloride solution were mixed with 2.5 ml of the aqueous choline oxidase solution (33.2 U/ml). The resulting solution was then placed in a crystallization dish and preincubated for 30 mins. at 37° C. in a shaking hood (100 r.p.m.).

(b) Glucose Oxidase System, Comparison System 2.5 ml of the aqueous glucose solution were mixed with 2.5 ml of the aqueous glucose oxidase solution (33.2 U/ml). The resulting solution was then placed in a crystallization dish and preincubated for 30 mins. at 37° C. in a shaking hood (100 r.p.m.).

4. Coloring of Hair

Coloring was carried out with each incubation mixture (points 3a and 3b) as described in Example 1.

100 g of the ready-to-use coloring system contained the quantity of choline oxidase or glucose oxidase which had an activity of 415 U under the conditions mentioned above in points 2b and 2d. In addition, 100 g of the ready-to-use coloring system contained the quantity of soya bean peroxidase which had an activity of 10.3 U under the conditions mentioned above in Example 1, point 2a.

The color obtained with the choline oxidase system was evaluated as 7A8 (fire red/red-orange). A Persian orange color (6A7) was obtained with the glucose oxidase system.

The color obtained with the choline oxidase system was distinctly more intensive and brilliant than the color obtained with the glucose oxidase system.

Example 3

Comparison of Choline Oxidase System and Xanthine Oxidase System

1. Preparation of the Coloring Cream

The coloring cream of Example 1 adjusted to pH 8.3 with ammonium hydroxide was used.

2. Preparation of the Enzyme Solutions

The peroxidase solution of Example 1 was used. In addition, the following solutions were prepared:

(a) Buffer Solution

The buffer solution of Example 2, point 2a, was used.

(b) Choline Oxidase Solution (8 U/ml), Invention

Powder-form choline oxidase from Alcaligenes species (Sigma: Catalog No. C-5896) was used to prepare the choline oxidase solution. The activity of the choline oxidase is defined thus: one unit [1 U] of choline oxidase forms 1 $\mu$mol $H_2O_2$ in 1 minute at pH 8.0/37° C. by oxidation of 1 $\mu$mol choline to betaine aldehyde.

Since the activity based on the weight (U/g) of the choline oxidase varies from batch to batch in the commercial products, the preparation of the solution is dependent on the activity of the choline oxidase supplied.

Choline oxidase with an activity of 14 U/mg Was used. 2 mg of this choline oxidase were dissolved in 2 ml of the buffer solution; 1.714 ml of this solution were removed and made up to 3 ml with the buffer solution. The solution had a pH of 8.3. The solution contains per milliliter the quantity of choline oxidase which has an activity of 8 U under the conditions mentioned above.

(c) Choline Chloride Solution, Invention 1.68 g of choline chloride were dissolved in 10 ml of the buffer solution. The pH value of the solution was 8.3.

(d) Xanthine Oxidase Solution (8.0 U/ml), Comparison System

Powder-form xanthine oxidase from microorganisms (Sigma: Catalog No. X-2252) was used to prepare the xanthine oxidase solution. The activity of the xanthine oxidase is defined thus: one unit [1 U] of xanthine oxidase oxidizes 1 $\mu$mol of xanthine to uric acid in one minute at pH 7.5/25° C.

Since the activity based on the weight (U/g) of the xanthine oxidase varies from batch to batch in the commercial products, the preparation of the solution is dependent on the activity of the xanthine oxidase supplied.

Xanthine oxidase with an activity of 8.6 U/mg was used. 3 mg of this xanthine oxidase were dissolved in 1 ml of buffer solution; 930.2 µl of this solution were removed and made up to 3 ml with buffer solution. The solution had a pH of 8.3. The solution contains per milliliter the quantity of xanthine oxidase which has an activity of 8 U under the conditions mentioned above.

(e) Xanthine Solution, Comparison System 0.0018 g xanthine were dissolved in 10 ml of buffer solution. The pH of the solution was 8.3.

3. Incubation Mixture (a) Choline Oxidase System, Invention 2.5 ml of the aqueous choline chloride solution were mixed with 2.5 ml of the aqueous choline oxidase solution (8 U/ml). The resulting solution was then placed in a crystallization dish and preincubated for 30 mins. at 37° C. in a shaking hood (100 r.p.m.).

(b) Xanthine Oxidase System, Comparison System 2.5 ml of the aqueous xanthine solution were mixed with 2.5 ml of the aqueous xanthine oxidase solution (8 U/ml). The resulting solution was then placed in a crystallization dish and preincubated for 30 mins. at 37° C. in a shaking hood (100 r.p.m.).

4. Coloring of Hair

Coloring was carried out with each incubation mixture as described in Example 1.

100 g of the ready-to-use coloring system contained the quantity of choline oxidase or xanthine oxidase which had an activity of 100 U under the conditions mentioned above in points 2b and 2d. In addition, 100 g of the ready-to-use coloring system contained the quantity of soya bean peroxidase which had an activity of 10.3 U under the conditions mentioned above in Example 1, point 2a.

The color tones were evaluated as described in Example 1.

The color obtained with the choline oxidase system was evaluated as 6A7 (Persian orange). A butter-yellow color (4A5) was obtained with the xanthine oxidase system.

The color obtained with the choline oxidase system according to the invention was distinctly more intensive and brilliant than the color obtained with the xanthine oxidase system.

Further Examples

The following colorings were carried out similarly to the procedure of Example 1:

| Secondary Intermediate | Color |
| --- | --- |
| 1 Coloring with 1-methyl-2,5-diaminobenzene as primary intermediate | |
| 1,3-Bis-(2,4-diaminophenoxy)-propane + 4HCl | 20F4 Ink blue |
| 2,4-Diaminophenoxy ethanol + 2 HCl | 20F5 Black-blue |
| 3-Amino-6-methoxy-2-methylaminopyridine + 2 HCl | 4F3 Olive brown |
| 1-Naphthol | 6E3 Grey-brown |
| 2,4-Dichloro-3-aminophenol | 13F2 Purple-grey |
| 2-Amino-3-hydroxypyridine | 8E3 Grey-brown |
| 5-Amino-4-chloro-2-methylphenol + HCl | 9D5 Rosewood |
| 5-Amino-2-methylphenol | 10E4 Violet-brown |
| Resorcinol | 4B5 Butter yellow |
| 3-Aminophenol | 4B5 Butter yellow |
| 2 Coloring with 1,4-diaminobenzene as primary intermediate | |
| 2,4-Diaminophenoxy ethanol + 2 HCl | 19F8 Black-blue |
| 4-Chlororesorcinol | 4B4 Champagne |
| 2-Methyl-5-aminophenol | 11C5 Grey-red |
| 3-Aminophenol | 4B4 Champagne |
| 2,7-Dihydroxynaphthalene | 4B4 Champagne |
| 3 Coloring with 2,4,5,6-tetraaminopyridine . $H_2SO_4$ as primary intermediate | |
| 2-Methyl resorcinol | 6A5 Salmon pink |
| 2,7-Dihydroxynaphthalene | 4B5 Wheat gold |
| 1-Methyl-2,6-bis-(2-hydroxyethylamino)-benzene | 12B8 Rose pink |
| 4 Coloring with 4-aminophenol as primary intermediate | |
| 5-Amino-2-methylphenol | 6B6 Grey-orange |
| 1-Naphthol | 6B3 Skin-colored |
| 1,3-Bis-(2,4-diaminophenoxy)-propane + 4 HCl | 8D4 Red-brown |
| 6-Hydroxyindole | 5C4 Gold-blond |
| 5 Coloring with 4-hydroxy-2,5,6-triaminopyrimidine as primary intermediate | |
| 2,4-Diaminophenoxyethanol + 2HCl | 16F6 Dark violet |
| 1,3-bis-(2,4-diaminophenoxy)-propane + 4HCl | 15F6 Dark violet |
| Resorcinol | 7C5 Brown-orange |
| 2-Methyl resorcinol (3x concentrated) | 8B5 Grey-red |
| 6 Coloring with N,N-bis-((3-hydroxyethyl)-1,4-diaminobenzene as primary intermediate | |
| 2,6-Dimethoxy-3,5-diaminopyridine | 23F8 Dark blue |
| 1-Methoxy-2-amino-4-(β-hydroxyethylamino)-benzene | 21F8 Dark blue |
| 5-Amino-4-chloro-2-methylphenol | 17F7 Dark violet |
| 3,4-Methylenedioxyaniline + HCl | 6E4 Brown |
| 7 Coloring with 1-(2'-hydroxyethyl)-2,5-diaminobenzene as primary intermediate | |
| 2-Chloro-6-methyl-3-aminophenol | 14F5 Dark purple |
| 2,4-Diaminophenoxyethanol + 2HCl | 20F5 Black-blue |
| 2-Methyl resorcinol | 5C4 Gold-blond |
| 3,4-Methylenedioxyaniline + HCl | 5C3 Red-blond |
| 2-Aminophenol | 4C4 Blond |
| 8 Coloring with 3-methyl-4-aminophenol as primary intermediate | |
| 3-Aminophenol | 4B4 Champagne |
| 3-Amino-6-methoxy-2-methylaminopyridine | 4B6 Grey-yellow |
| 2-Amino-3-hydroxypyridine | 5C4 Gold-blond |
| 1-Methoxy-2-amino-4-(β-hydroxyethylamino)-benzene | 9E4 Red-brown |
| 5-Amino-2-methylphenol | 6B7 Carrot red |
| 9 Coloring with 4-amino-2-aminopmethylphenol . 2 HCl as primary intermediate | |
| 2-Chloro-6-methyl-3-aminophenol | 7B7 Red-orange |
| 2,4-Diaminophenoxyethanol + 2HCl | 9D5 Rosewood |
| 2,6-Dimethoxy-3,5-diaminopyridine | 27F4 Dark green |
| 2-Aminophenol | 4A5 Butter yellow |
| 10 Coloring with 1,8-bis-(2,5-diaminophenoxy)-3,6-dioxaoctane as primary intermediate | |
| 3-Amino-6-methoxy-2-methylaminopyridine | 5E3 Mouse grey |
| 1,3-Bis-(2,4-diaminophenoxy)-propane + 4 HCl | 20E4 Turkish blue |

What is claimed is:

1. A composition for coloring keratin fibers comprising (a) at least one dye precursor;

(b) a choline-based oxidase system comprising choline oxidase, or reaction products thereof, or combinations thereof; and (c) at least one peroxidase.

2. The composition of claim 1, wherein the choline oxidase is produced by Alcaligenes species or *Arthrobacter globiformis* or combinations thereof.

3. The composition of claim 2 wherein the dye precursor is a primary intermediate oxidation dye precursor.

4. The composition of claim 3, wherein the primary intermediate comprises p-phenylenediamine, p-toluylenediamine, p-aminophenol, 1-(2'-hydroxyethyl)-2, 5-diaminobenzene, 4-amino-3-methylphenol, 2,4,5,6-tetraaminopyrimidine, 2-hydroxy-4,5,6-triaminopyrimidine, 4-hydroxy-2,5,6-triaminopyrimidine, 4,5-diamino-1-(2-hydroxyethyl)-pyrazole, 2-aminomethyl-4-aminophenol, N,N-bis-(2-hydroxyethyl)-p-phenylenediamine, bis-(2-hydroxy-5-aminophenyl)-methane or o-aminophenol, or combinations thereof.

5. The composition of claim 4, further comprising at least one secondary intermediate selected from the group consisting of 1-naphthol, 1,5-dihydroxynaphthalene, 2,7-dihydroxynaphthalene, 1,7-dihydroxynaphthalene, 5-amino-2-methylphenol, resorcinol, 1,3-bis-(2,4-diaminophenoxy)-propane, 2,4-dichloro-3-aminophenol, 4-chlororesorcinol, 2-amino-3-hydroxypyridine, 2,6-dimethoxy-3,5-diaminopyridine, 2-chloro-6-methyl-3-aminophenol, 2-methyl-4-chloro-5-aminophenol, 2-methyl resorcinol, 5-methyl resorcinol, 2,5-dimethyl resorcinol, 2,6-bis-(2-hydroxyethylamino)-toluene, 2,6-dihydroxy-3,4-diaminopyridine, 3-amino-2-methylamino-6-methoxypyridine, 2,4-diaminophenoxy ethanol, 1-methoxy-2-amino-4-(2-hydroxyethylamino)-benzene, 6-methyl-1,2,3,4-tetrahydroquinoxaline, 3,4-methylenedioxy aniline, m-aminophenol, o-aminophenol and 2-chlororesorcinol.

6. The composition of claim 5 wherein the dye precursor comprises at least one primary intermediate and secondary intermediate combination of (i) p-aminophenol and 5-amino-2-methylphenol, (ii) 1-methyl-2,5-diaminobenzene and 2,4-diaminophenoxyethanol, (iii) 4-amino-2-aminomethylphenol and 2-chloro-6-methyl-3-aminophenol, (iv) 4-amino-2-aminomethylphenol and 2,4-diaminophenoxy ethanol, (v) 1-methyl-2,5-diaminobenzene and 5-amino-2-methylphenol, (vi) 1-methyl-2,5-diaminobenzene and 1,3-bis-(2,4-diaminophenoxy)-propane, (vii) 4-hydroxy-2,5,6-triaminopyrimidine and 2-methylresorcinol, (viii) 1-(β-hydroxyethyl)-2,5-diaminobenzene and 2,4-diaminophenoxy ethanol, or (ix) N,N-bis-(β-hydroxyethyl)-1,4-diaminobenzene and 1-methoxy-2-amino-4-(2-hydroxyethylamino)-benzene.

7. The composition of claim 1, wherein the dye precursor is an indoline compound corresponding to formula (Ia), or a physiologically compatible salt of the indoline of formula (Ia):

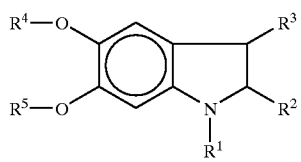

(Ia)

wherein, independently of one another, $R^1$ is hydrogen, a $C_{1-4}$ alkyl group or a $C_{1-4}$ hydroxyalkyl group, $R^2$ is hydrogen or a —COOH group, wherein the —COOH group may optionally be a salt having a physiologically compatible cation, $R^3$ is hydrogen or a $C_{1-4}$ alkyl group, and $R^4$ and $R^5$ are, independently of one another, hydrogen, a $C_{1-4}$ alkyl group or a —CO—$R^6$ group, wherein $R^6$ is a $C_{1-4}$ alkyl group.

8. The composition of claim 1, wherein the dye precursor is an indole compound corresponding to formula (Ib) or a physiologically compatible salt of the indole of formula (Ib):

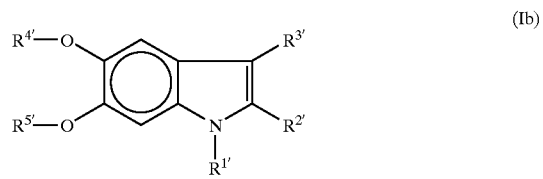

(Ib)

wherein, independently of one another, $R^{1'}$ is hydrogen, a $C_{1-4}$ alkyl group or a $C_{1-4}$ hydroxyalkyl group, $R^{2'}$ is hydrogen or a —COOH group, wherein the —COOH group may optionally be a salt having a physiologically compatible cation, $R^{3'}$ is hydrogen or a $C_{1-4}$ alkyl group, and $R^{4'}$ and $R^{5'}$ are, independently of one another, hydrogen, a $C_{1-4}$ alkyl group or a —CO—$R^{6'}$ group, wherein $R^{6'}$ is a $C_{1-4}$ alkyl group.

9. The composition of claim 1 wherein the peroxidase is obtained from plants or fungi.

10. The composition of claim 9, wherein the peroxidase comprises a soya bean peroxidase.

11. The composition of claim 1, wherein the composition has a pH value of 7 to 10.

12. The composition of claim 11, wherein the pH value is about 8.3.

13. The composition of claim 1 further comprising at least one surfactant.

14. The composition of claim 13 wherein the surfactant comprises a nonionic surfactant or an amphoteric surfactant, or combinations thereof.

15. The composition of claim 13 wherein the surfactant comprises at least one anionic surfactant and at least one amphoteric surfactant, or at least one nonionic surfactant, or combinations thereof.

16. The composition of claim 1 wherein the choline oxidase is produced by Alcaligenes species or *Arthrobacter globiformis* or combinations thereof, wherein the peroxidase is obtained from plants or fungi and wherein the dye precursor comprises a primary intermediate oxidation dye precursor, a derivative of an indole, or a derivative of an indoline, or combinations thereof.

17. The composition of claim 16 wherein the composition has a pH value of 7 to 10.

18. The composition of claim 17 further comprising at least one surfactant wherein the surfactant comprises a nonionic surfactant, an amphoteric surfactant, or combinations thereof.

19. The composition of claim 18 wherein the dye precursor further comprises a secondary intermediate dye precursor.

20. A process for coloring keratin containing fibers comprising
  (a) forming a composition comprising
    (i) at least one dye precursor;
    (ii) a choline-based oxidase system comprising choline oxidase, or reaction products thereof, or combinations thereof; and
    (iii) at least one peroxidase; and
  (b) applying the composition to keratin containing fibers.

21. The process of claim 20 further comprising incubating the choline-based oxidase system for 30 minutes at 37° C. prior to forming the composition.

* * * * *

UNITED STATES PATENT AND TRADEMARK OFFICE
CERTIFICATE OF CORRECTION

PATENT NO.    : 6,630,003 B1                                    Page 1 of 1
DATED         : October 7, 2003
INVENTOR(S)   : Saettler et al.

It is certified that error appears in the above-identified patent and that said Letters Patent is hereby corrected as shown below:

<u>Title page,</u>
Item [86] PCT No., after "§ 371 (c)(1), (2), (4) Date:" delete "Aug. 21, 2001", and insert therefore -- Aug. 22, 2001 --.

Signed and Sealed this

Twelfth Day of October, 2004

JON W. DUDAS
*Director of the United States Patent and Trademark Office*